(12) United States Patent
Gutierrez et al.

(10) Patent No.: US 10,507,306 B2
(45) Date of Patent: Dec. 17, 2019

(54) BACKLOADABLE OPTICAL SHAPE SENSING GUIDEWIRES

(75) Inventors: Luis Felipe Gutierrez, Jersey City, NJ (US); Robert Manzke, Sleepy Hollow, NY (US); Raymond Chan, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 13/819,427

(22) PCT Filed: Aug. 29, 2011

(86) PCT No.: PCT/IB2011/053774
§ 371 (c)(1),
(2), (4) Date: Feb. 27, 2013

(87) PCT Pub. No.: WO2012/029013
PCT Pub. Date: Mar. 8, 2012

(65) Prior Publication Data
US 2013/0158512 A1  Jun. 20, 2013

Related U.S. Application Data

(60) Provisional application No. 61/378,967, filed on Sep. 1, 2010.

(51) Int. Cl.
*A61B 5/00* (2006.01)
*A61M 25/09* (2006.01)
(Continued)

(52) U.S. Cl.
CPC ............ *A61M 25/09* (2013.01); *A61B 34/20* (2016.02); *A61M 25/09041* (2013.01);
(Continued)

(58) Field of Classification Search
CPC ............ A61B 2034/2061; A61B 5/084; A61B 5/6852; A61B 1/00165; A61B 1/00167;
(Continued)

(56) References Cited

U.S. PATENT DOCUMENTS 5,018,823 A   5/1991  Himmelwright
5,748,820 A   5/1998  Le Marer et al.
(Continued)

FOREIGN PATENT DOCUMENTS

| CN | 1667441 A | 9/2005 |
| JP | 2008190910 A | 8/2008 |
| WO | 2005087128 | 9/2005 |

OTHER PUBLICATIONS

Etsuji Sugita et al. "SC-Type Single-Mode Optical Fiber Connectors." Journal of Lighwave Technology. IEEE Service Center, New York. vol. 7, No. 11, Nov. 1, 1989, pp. 1689-1696.
(Continued)

*Primary Examiner* — Max F Hindenburg

(57) ABSTRACT

An optical guidewire system employs an optical guidewire (10), an optical guidewire controller (12), a guide interface (13) and an optical connector (15). The optical guidewire (10) is for advancing a catheter (20) to a target region relative to a distal end of the optical guidewire (10), wherein the optical guidewire (10) includes one or more guidewire fiber cores (11) for generating an encoded optical signal (16) indicative of a shape of the optical guidewire (10). The optical guidewire controller (12) is responsive to the encoded optical signal (16) for reconstructing the shape of the optical guidewire (10). The guidewire interface (13) includes one or more interface fiber core(s) (14) optically coupled to the optical guidewire controller (12). The optical connector (15) facilitates a connection, disconnection and reconnection of the optical guidewire (10) to the guidewire
(Continued)

interface (13) that enables a backloading the catheter (20) on the optical guidewire (10).

15 Claims, 9 Drawing Sheets

(51) Int. Cl.
    *A61B 34/20*     (2016.01)
    *G02B 6/02*     (2006.01)
    *G02B 6/38*     (2006.01)

(52) U.S. Cl.
    CPC ............... *A61B 2034/2061* (2016.02); *A61M 2205/0244* (2013.01); *A61M 2205/3592* (2013.01); *A61M 2205/502* (2013.01); *G02B 6/02042* (2013.01); *G02B 6/02076* (2013.01); *G02B 6/3831* (2013.01); *G02B 6/3846* (2013.01); *G02B 6/3878* (2013.01); *G02B 6/3895* (2013.01)

(58) Field of Classification Search
    CPC ............... A61B 1/0017; A61M 25/09; A61M 25/09016; A61M 25/09025; A61M 25/09033; G02B 6/02042; G02B 6/02076; G02B 6/3831; G02B 6/3846; G02B 6/3878; G02B 6/3895
    USPC ......................................................... 600/585
    See application file for complete search history.

(56) References Cited

U.S. PATENT DOCUMENTS

| | | | |
|---|---|---|---|
| 5,813,405 A | | 9/1998 | Montano et al. |
| 6,312,314 B2* | | 11/2001 | Cheetham et al. ............... 451/6 |
| 6,749,344 B2 | | 6/2004 | Hamm et al. |
| 6,868,195 B2 | | 3/2005 | Fujita |
| 8,182,433 B2 | | 5/2012 | Len et al. |
| 9,500,472 B2 | | 11/2016 | Ramamurthy et al. |
| 2001/0021843 A1 | | 9/2001 | Bosselmann et al. |
| 2003/0135102 A1* | | 7/2003 | Burdette et al. ............ 600/407 |
| 2004/0165810 A1* | | 8/2004 | Fujita ................. A61B 1/0055 385/12 |
| 2006/0013523 A1 | | 1/2006 | Childlers et al. |
| 2007/0065077 A1 | | 3/2007 | Childlers et al. |
| 2008/0262442 A1 | | 10/2008 | Carlin et al. |
| 2008/0285909 A1 | | 11/2008 | Younge et al. |
| 2009/0123111 A1 | | 5/2009 | Udd |
| 2010/0113942 A1* | | 5/2010 | Eberle ........................ 600/478 |

OTHER PUBLICATIONS

H.Y. Hsu, A.J. Hariz, T. Omari, M.F. Teng, D. Sii, S. Chan, L. Lau, S. Tan, G.Lin, M. Haskard, D. Mulcahy, M. Bakewell. "Development of a MEMS Based Manometric Catheter for Diagnosis of Functional Swallowing Disorders." Journal of Physics: Conference Series 34 (2006) 955-960. International MEMS Conference 2006. Australia.

RRA Syms, H Zou, J Yao, D Uttamchandani, J Stagg. "Scalable electrothermal MEMS actuator for optical fibre alignment." Journal of Micromechanics and Microengineering 14 (2004) 1633-1639.

Brian Morgan, Jonathan McGee, Reza Ghodssi. "Automated Two-Axes Optical Fiber Alignment Using Grayscale Technology." Journal of Microlectromechanical Systems, vol. 16, No. 1, Feb. 2007. Washington DC.

RRA Syms, H Zou, J Stagg. "Micro-opto-electro-mechanical systems alignment stages with Vernier latch mechanisms." Journal of Optics A: Pure and Applied Optics 8 (2006) S305-S312.

V.A. Henneken, M. Tichem, P.M. Sarro. "In-package MEMS-based thermal actuators for micro-assembly." Journal of Micromechanics and Microengineering 16 (2006) S107-S115. The Netherlands.

John M. Haake, Robert L. Wood, Vijayakumar R. Duhler. "In-Package Active Fiber Optic Micro-Aligner." IEEE Conference Publication May 25-28, 1998, pp. 1446-1449. Seattle, WA.

A. Unamuno, D. Uttamchandani. "MEMS variable optical attenuator with vernier latching mechanism." IEEE Photonics Technology Letters. vol. 18, 2006, pp. 88-90.

M.W. Beranek, E.Y. Chan, H.E. Hager, Q.N. Le, B. Co, W.A. Seattle. "Status of optoelectronic module packaging for avionics/aerospaceapplications." IEE Lasers and Electro-optics Society Annual Meeting. 1998. LEOS'98, 1998.

E.V. White, M.D. Rogers, J.M. Haake. "Three-axis microactuator for smart optical interconnect system." Proceedings of SPIE, 1998, p. 353.

* cited by examiner

BACKLOADABLE OPTICAL SHAPE SENSING GUIDEWIRES

The present invention generally relates to guidewires for advancing catheters to a target region during a minimally invasive intervention (e.g., a guidewire for advancing a catheter to a heart during a minimally invasive cardiovascular intervention). The present invention specifically relates to optical shape sensing guidewires having optical connectors for facilitating a backloading of catheters over a proximal end of the guidewires.

Many minimally invasive cardiovascular interventions are performed with catheters, which are long thin tubes that can be advanced through the blood vessels with diagnostic or therapeutic payloads (e.g., contrast agents, pressure transducers, balloon, stents, etc.). Due to a variety of reasons (e.g., tortuosity of vessel shape or vessel blockages), a guidewire may be advanced to a target region of the intervention prior to an introduction of the diagnostic or therapeutic catheter. The guidewire is typically a thin wire with specifically designed material properties that facilitates a loading of the diagnostic or therapeutic catheter over a proximal end of the guidewire and an advancement of the catheter over the guidewire to reach the target region.

These procedures are generally guided with real-time X-ray imaging, which depicts two-dimensional ("2D") projection images of the catheters and guidewires. However, challenges with X-ray imaging include the 2D nature of the imaging and the ionizing radiation to the patient and physician. A more viable alternative is optical shape sensing technology, which may provide full three-dimensional ("3D") shape information of medical instruments without the need for any harmful radiation. This technology has been described in U.S. Patent Application Publications 2006/0013523 A1 and 2007/0065077 A1 and has been proposed for integration into medical instruments (e.g., guidewires and catheters) in U.S. Patent Application Publication US 2008/0285909 A1.

Based on this technology, one way to implement spatially sensitive bend and twist sensing using optical fibers is to combine multiple cores of fiber-bragg-grating ("FBG") fibers in specific geometric orientations over distance. One potential setup may be three (3) or more FBG fibers oriented in a helical structure including an additional FBG fiber in the helix center. For creating a medical guidewire, such multicore fiber would need to be integrated with a sheathing material designed to meet medical requirements in terms of biocompatibility and mechanical properties.

In the many cases where guidewires are needed to reach the target region prior to advancing the catheter, it would be desirable to use the shape sensing capabilities during the guidewire phase prior to the backloading of the catheter. However, in order to enable the guidewire with the shape sensing capability, it needs to be connected to an optical system at the point where the backloading would normally occur. Of course, the guidewire could be temporarily disconnected from the optical system during backloading, but current optical connectors are much too large to allow a catheter to be passed over them. Alternatively, the point at which the guidewire meets the connector could be completely severed to allow backloading, but then no more shape sensing could be performed with the guidewire and such severance of the guidewire may not be desirable in many interventions.

The present invention proposes optical connectors for guidewires that may be reversibly unplugged while still being small enough to allow standard catheters to be backloaded onto the guidewire prior to re-establishing the optical connection for continued shape sensing of the guidewire.

One form of the present invention is an optical guidewire system employing an optical guidewire, an optical guidewire controller, a guidewire interface and an optical connector. The optical guidewire is for advancing a catheter to a target region relative to a distal end of the optical guidewire. To this end, the optical guidewire includes one or more guidewire fiber cores for generating an encoded optical signal indicative of a shape of the optical guidewire. The optical guidewire controller is responsive to the encoded optical signal for reconstructing the shape of the optical guidewire, and the guidewire interface includes one or more interface fiber cores optically coupled to the optical guidewire controller. In operation, the optical connector facilitates a connection of the optical guidewire to the guidewire interface to optically communicate the encoded optical signal from the guidewire fiber core(s) through the interface fiber core(s) to the optical guidewire controller. Subsequent to the connection of the optical guidewire to the guidewire interface, the optical connector facilitates a disconnection of the optical guidewire from the guidewire interface and a loading of the catheter on a proximal end of the optical guidewire. Subsequent to a disconnection of the optical guidewire from the guidewire interface and a loading of the catheter on a proximal end of the optical guidewire, the optical connector facilitates a reconnection of the optical guidewire to the guidewire interface to recommunicate the optical encoded optical signal from the guidewire fiber core(s) through the interface fiber core(s) to the optical guidewire controller.

Another form of the present invention is a method for advancing a catheter to a target region relative to a distal end of an optical guidewire including one or more guidewire fiber cores for generating an encoded optical signal indicative of a shape of the optical guidewire. The method involves a connection of the optical guidewire to a guidewire interface to optically communicate the encoded optical signal from the guidewire fiber core(s) through one or more interface fiber cores to an optical guidewire controller. The guidewire interface includes the interface fiber core(s) optically coupled to the optical guidewire controller, which is responsive to the encoded optical signal for reconstructing the shape of the optical guidewire. Subsequent to the connection of the optical guidewire to the guidewire interface, the optical connector facilitates a disconnection of the optical guidewire from the guidewire interface and a loading of the catheter on a proximal end of the optical guidewire. Subsequent to a disconnection of the optical guidewire from the guidewire interface and a loading of the catheter on a proximal end of the optical guidewire, the optical connector facilitates a reconnection of the optical guidewire to the guidewire interface to recommunicate the optical encoded optical signal from the guidewire fiber core(s) through the interface fiber core(s) to the optical guidewire controller.

The foregoing forms and other forms of the present invention as well as various features and advantages of the present invention will become further apparent from the following detailed description of various exemplary embodiments of the present invention read in conjunction with the accompanying drawings. The detailed description and drawings are merely illustrative of the present invention rather than limiting, the scope of the present invention being defined by the appended claims and equivalents thereof.

Figure 4A:
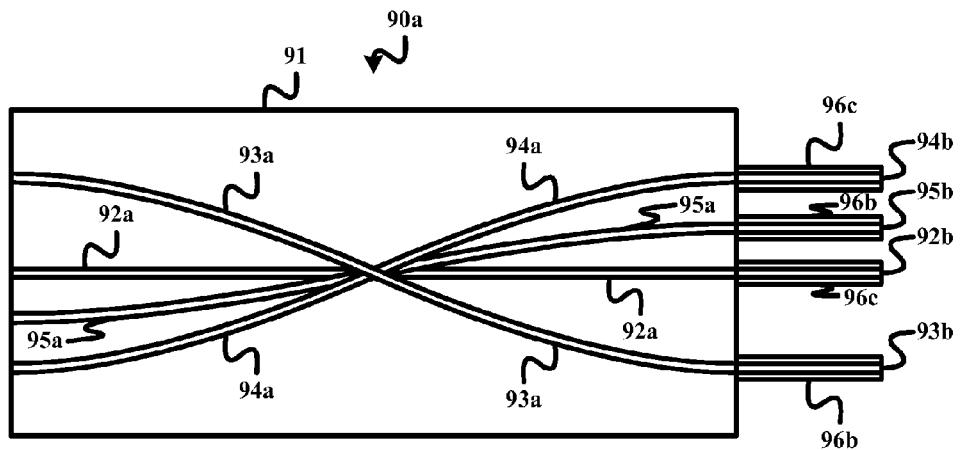
FIGS. 4A and 4B illustrate exemplary embodiments of an optical fiber in accordance with the present invention.
Figure 5A:
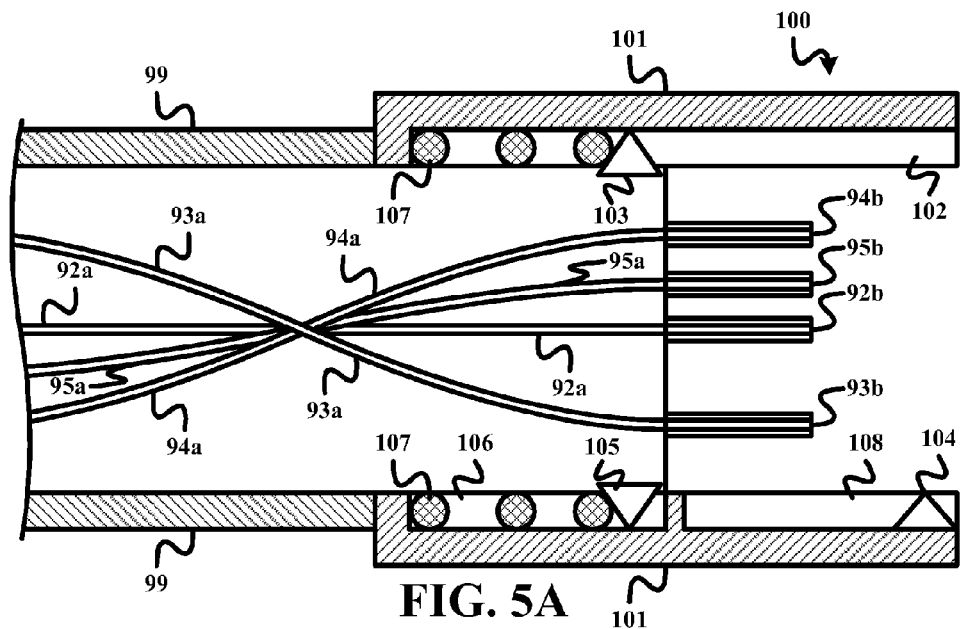
FIGS. 5A-5C illustrate an exemplary embodiment of an optical connector in accordance with the present invention.
Figure 6A:
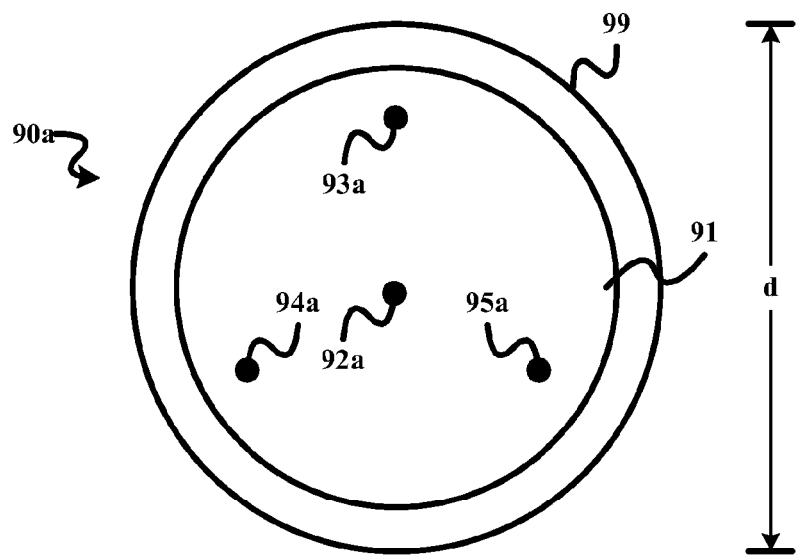
Figure 6B:
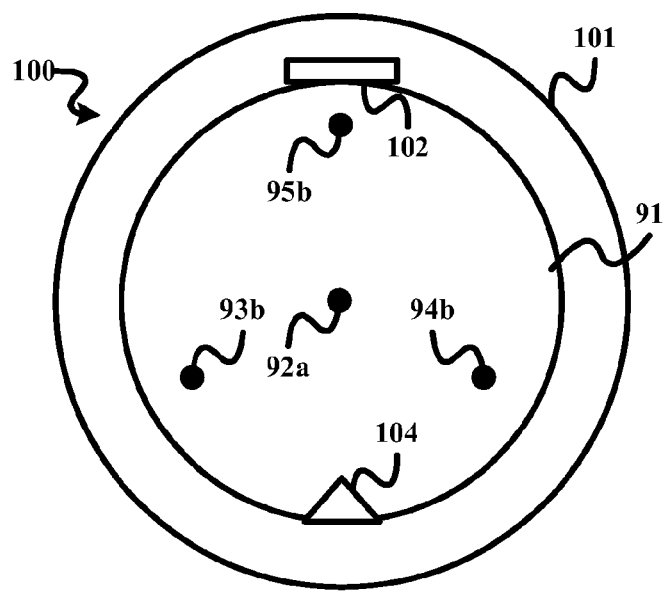

FIGS. 6A and 6B respectively illustrates a distal end and a proximal end of one embodiment of an optical guidewire shown in FIG. 5A incorporating the optical connector shown in FIG. 4A.

Figure 7A:
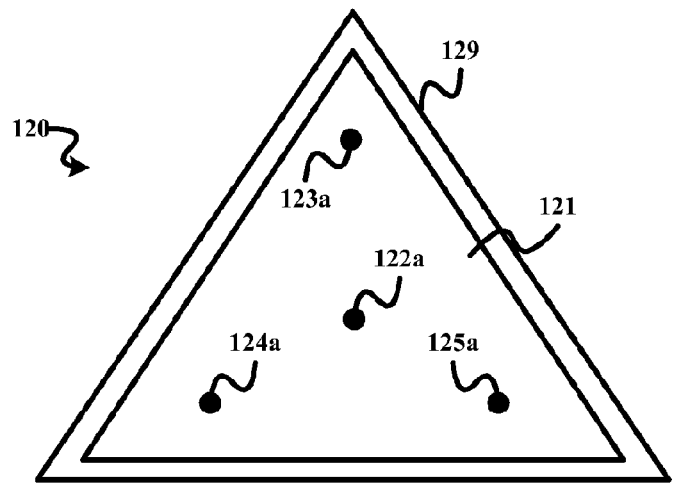
Figure 7B:
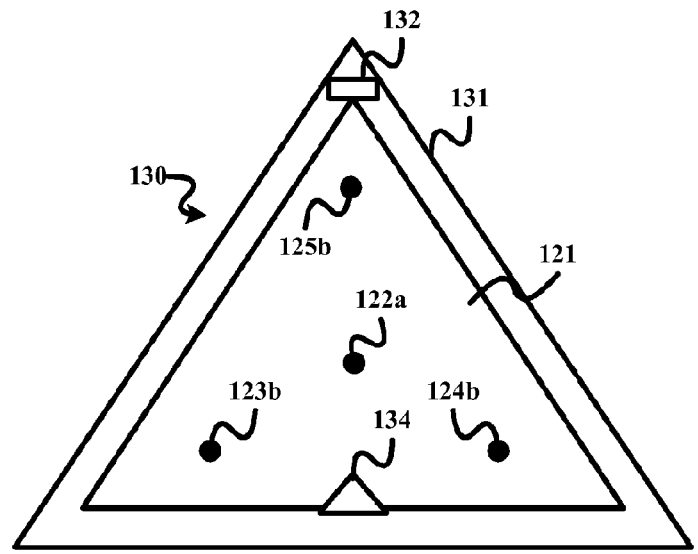

FIGS. 7A and 7B respectively illustrates a distal end and a proximal end of a second exemplary embodiment of an optical guidewire incorporating an optical connector in accordance with the present invention.

Figure 8A:
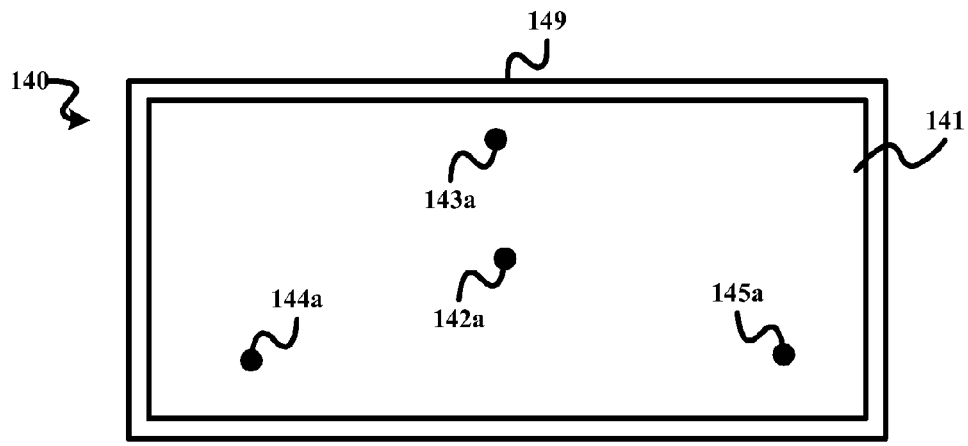
Figure 8B:
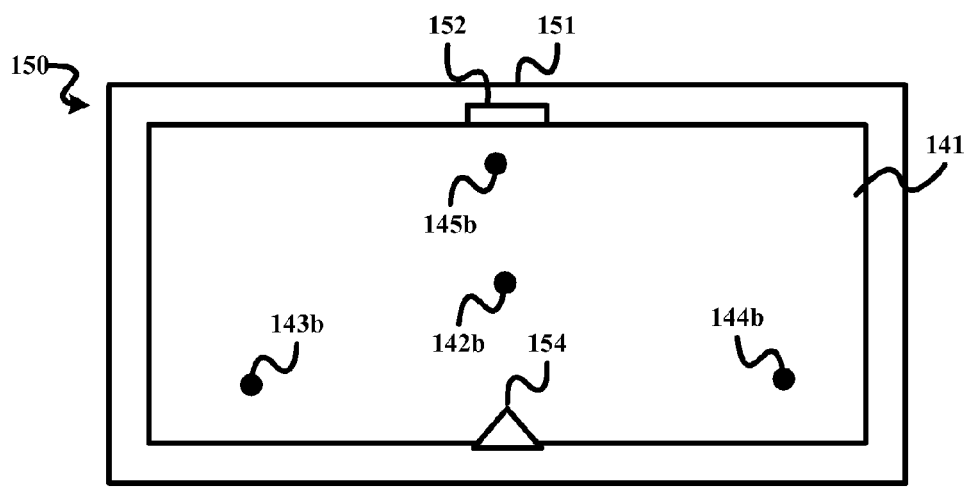

FIGS. 8A and 8B respectively illustrates a distal end and a proximal end of a third exemplary embodiment of an optical guidewire incorporating an optical connector in accordance with the present invention.

As shown in FIG. 1, an optical guidewire system of the present invention employs an optical guidewire 10, an optical guidewire controller 12, a guidewire interface 13 and an optical connector 15.

Optical guidewire 10 employs an optical fiber encircled by a sheath with the optical fiber including a cladding supporting one or more guidewire fiber cores 11. In an alternative embodiment not shown, optical guidewire 10 may employ two or more single core optical fibers, two or more multiple-core optical fibers or any combination thereof.

For purposes of the present invention, an optical fiber is broadly defined herein as any article or device structurally configured for transmitting light by means of successive internal optical reflections via fiber core(s), and a fiber core is broadly defined herein as any article structurally configured for reflecting a particular wavelength of light while transmitting all other wavelengths of light whereby the reflection wavelength may be shifted as a function of an external stimulus applied to optical fiber. Examples of an optical fiber and a fiber core include, but are not limited to, a flexible optically transparent glass or plastic fiber incorporating an array of fiber Bragg gratings integrated along a length of the fiber as known in the art, and a flexible optically transparent glass or plastic fiber having naturally variations in its optic refractive index occurring along a length of the fiber as known in the art.

In operation with a distal end 10a of optical guidewire 10 being manually or mechanically navigated guided to a target region during a minimally invasive intervention as known in the art, optical guidewire 10 generates an encoded optical signal 16 via guidewire fiber cores 11 as known in the art that indicates a shape of optical guidewire 10 at any instantaneous shape sampling of optical guidewire 10 and more particularly over the course of multiple shape samplings, encoded optical signal 16 indicates each change to the shape of optical guidewire 10 that occurs as the distal end of optical guidewire 10 is being navigated to the target region.

Optical guidewire controller 12 incorporates an optical interface (not shown) and a shape reconstructor (not shown) for processing encoded optical signal 16 to thereby periodically reconstruct a portion or an entire shape of optical guidewire 10. For purposes of the present invention, the optical interface is broadly defined herein as any device or system structurally configured for transmitting light through optical guidewire 10 to receive encoded optical signal 16 as generated by the successive internal reflections of the transmitted light via guidewire fiber core(s) 11. An example of the optical interface includes, but is not limited to, an arrangement of an optical coupler, a broadband reference reflector and a frequency domain reflectometer as known in the art for transmitting light through optical guidewire 10 and for receiving encoded optical signal 16 as generated by the successive internal reflections of the transmitted light via guidewire fiber core(s) 11.

For purposes of the present invention, the shape reconstructor is broadly defined as any article or device structurally configured for processing encoded optic signal 16 to partially or entirely reconstruct the shape of optical guidewire 10 and for generating fiber shape data in an appropriate form that enables an imaging system (e.g., an X-ray system, a MRI system, a CT system, an US system or a IVUS system) to visually display an instantaneous position and orientation of optical guidewire and more particularly, a movement tracking of optical guidewire 10. An example of the shape reconstructor includes, but is not limited to, a reconstruction engine installed as software and/or firmware on any type of computer for implementing a known shape reconstruction technique. In particular, a known shape reconstruction technique for correlating encoded optic signal 16 into strain/bend measurements that are integrated into a shape of optical guidewire 10. In practice, the reconstruction engine may or may not be integrated into the imaging system.

Figure 1A:
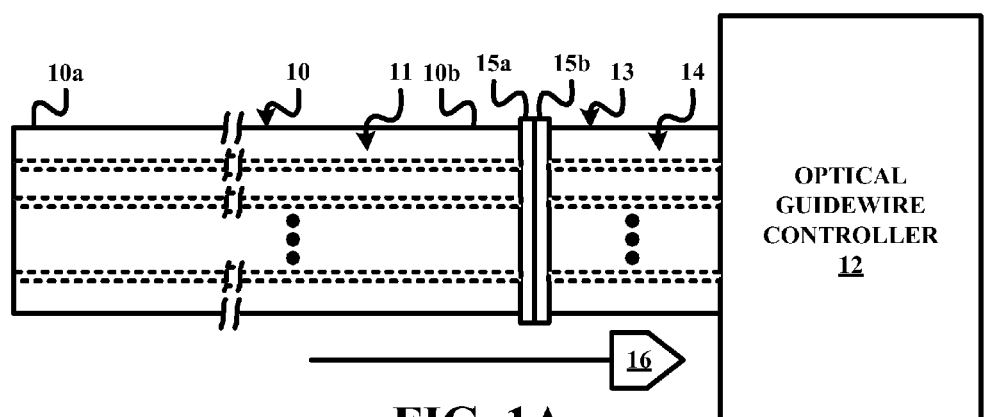
FIGS. 1A-1C illustrate an exemplary optical guidewire method in accordance with the present invention.

For purposes of the present invention, a guidewire interface is broadly defined as any article or device structurally configured for optically coupling optical guidewire 10 and optical guidewire controller 12 when connected to optical guidewire 10. For example, as shown in FIGS. 1A and 1C, guidewire interface 13 may employ an optical fiber extending from optical connector 15 and optically coupled to optical guidewire controller 12. The optical fiber is a cladding encircled by a protective layer and supporting one or more interface fiber cores 14 optically coupled to optical guidewire controller 12. In an alternative embodiment not shown, guidewire interface 13 may employ one or more single core optical fibers, one or more multiple-core optical fibers, or any combination thereof extending from optical connector 15 and optically coupled to optical guidewire controller 12. In a further alternative embodiment, guidewire interface 13 may include one or more optical fibers, each being single core or multiple-core, fully embedded within optical connector 15 and optically coupled to optical guidewire controller 12.

Optical connector 15 employs a guidewire connector 15a coupled to guidewire 10 and an interface connector 15b coupled to guidewire interface 13. For purposes of the present invention, optical connector 15 is broadly defined as any article or device for selectively connecting and disconnecting an optical guidewire and a guidewire interface of the present invention.

As shown in FIG. 1A, optical connector 15 facilitates a connection of optical guidewire 10 to guidewire interface 13 for optically coupling fiber cores 11 and 14 whereby encoded optical signal 16 is transmitted from guidewire fiber core(s) 11 through interface fiber core(s) 14 to optical guidewire controller 12. As a result, optical guidewire controller 12 partially or entirely reconstructs a shape of optical guidewire 10 as distal end 10a of optical guidewire 10 is navigated to a target region.

Figure 1B:
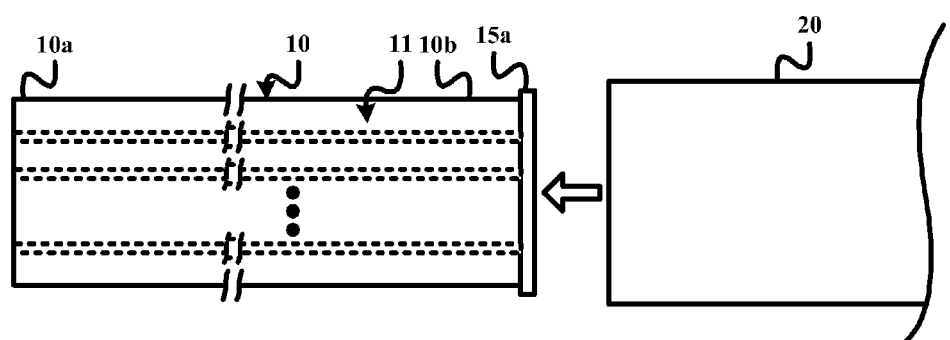
Figure 1C:
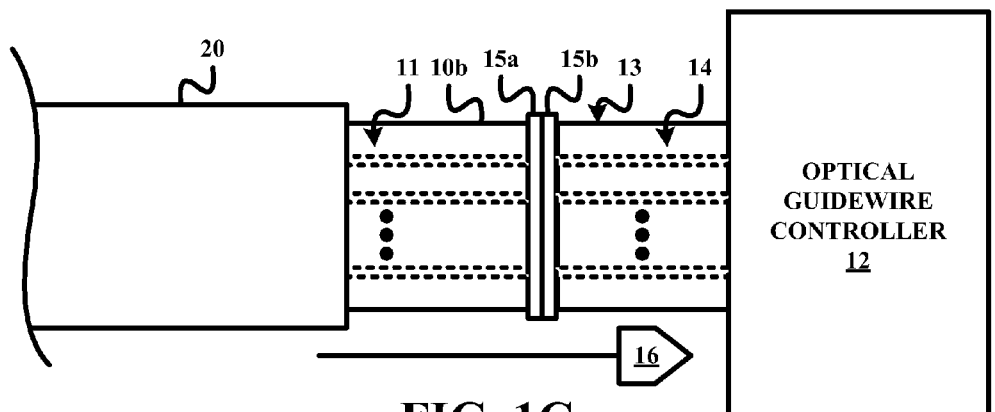

As shown in FIG. 1B, upon the distal end 10a being positioned relative to the target region, optical connector 15 facilitates a disconnection of optical guidewire 10 from guidewire interface 13 whereby a catheter 20 may be loaded on a proximal end 10b of optical guidewire 10. In practice, the catheter 20 may be partially or fully extend along optical guidewire 10 upon being loaded upon optical guidewire 10.

As shown in FIG. 1C, optical connector 15 facilitates a reconnection of optical guidewire 10 to guidewire interface 13 for again optically coupling fiber cores 11 and 14 whereby encoded optical signal 16 is again transmitted from guidewire fiber core(s) 11 through interface fiber core(s) 14 to optical guidewire controller 12. As a result, optical guidewire controller 12 may partially or entirely reconstruct a shape of optical guidewire 10 having catheter 20 loaded thereon.

Figure 2:
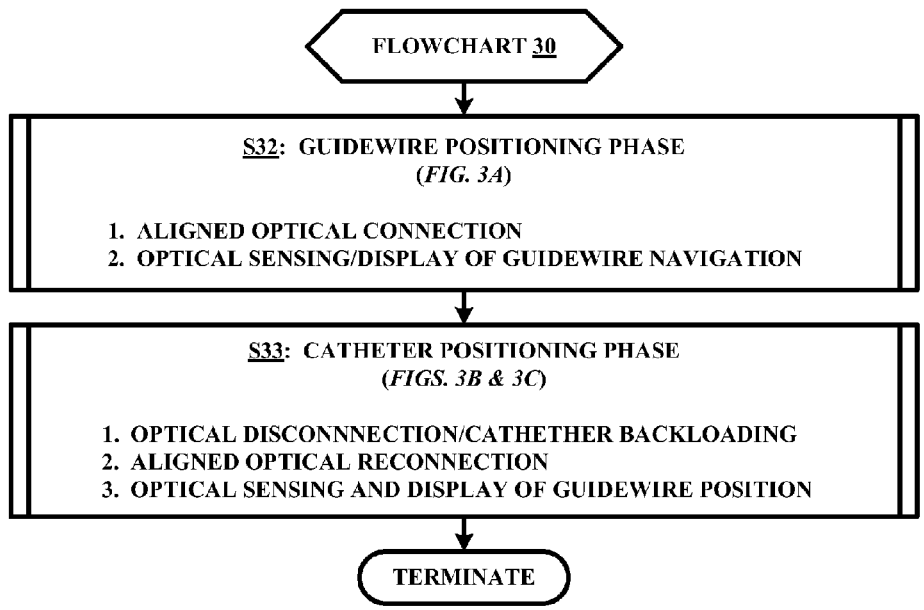
FIG. 2 illustrates a flowchart representative of an exemplary embodiment of an optical guidewire method in accordance with the present invention.

To facilitate a further understanding of the present invention, FIG. 2 illustrates a flowchart 30 representative of an optical guide method of the present invention.

A stage S32 of flowchart 30 encompasses an aligned optical connection of an optical guidewire and a guidewire interface, and an optical sensing and display of a navigation of the optical guidewire to a target region.

Figure 3A:
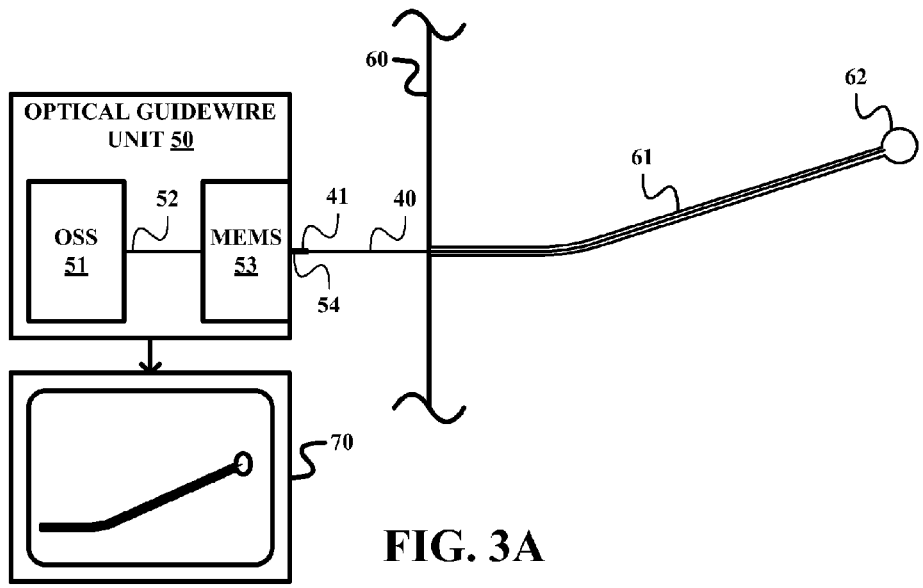
FIGS. 3A-3C illustrates an exemplary implementation of a minimally invasive intervention in accordance with the flowchart shown in FIG. 2.

For example, as shown in FIG. 3A, guidewire interface includes a multi-core interface optical fiber 52 and a microelectromechanical system ("MEMS") 53 as known in the art (e.g., a micro actuator based on thermal expansion in semiconductors, Vernier latches etc.), and an optical connector includes a snap plug 41 coupled to a multi-core optical guidewire 40 and a snap plug 54 coupled to interface optical fiber 52. During stage S32, plugs 41 and 54 are snapped together to optically couple the fiber cores of optical guidewire 40 and interface optical fiber 52 with MEMS 53 operating to facilitate a proper optical alignment of the fiber cores. Thereafter, a distal end of optical guidewire 40 is manually or mechanically navigated through tissue 60 via a vessel 61 relative to a target region 62. For example, the distal end of optical guidewire 40 may be manually or mechanically navigated through skin tissue via an artery to be positioned at any point within the artery whereby a catheter may be positioned and further navigated as needed to reach a heart. As optical guidewire 40 is navigated, optical guidewire controller 51 operates to partially or entirely reconstruct the shape of optical guidewire 40 whereby an imaging system 70 (e.g., an X-ray system, a MRI system, a CT system, an US system or an IVUS system) may display an overlay of optical guidewire within a scan image of target region 62.

A stage S33 of flowchart 30 encompasses a disconnection of plugs 41 and 54 to facilitate a backloading of a catheter onto the optical guidewire, an aligned optical re connection of the optical guidewire and the guidewire interface, and an optical sensing and display of the catheter as loaded on the optical guidewire.

Figure 3B:
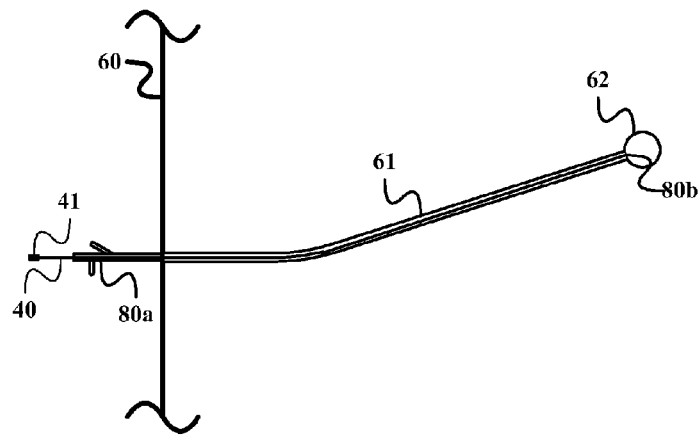
Figure 3C:
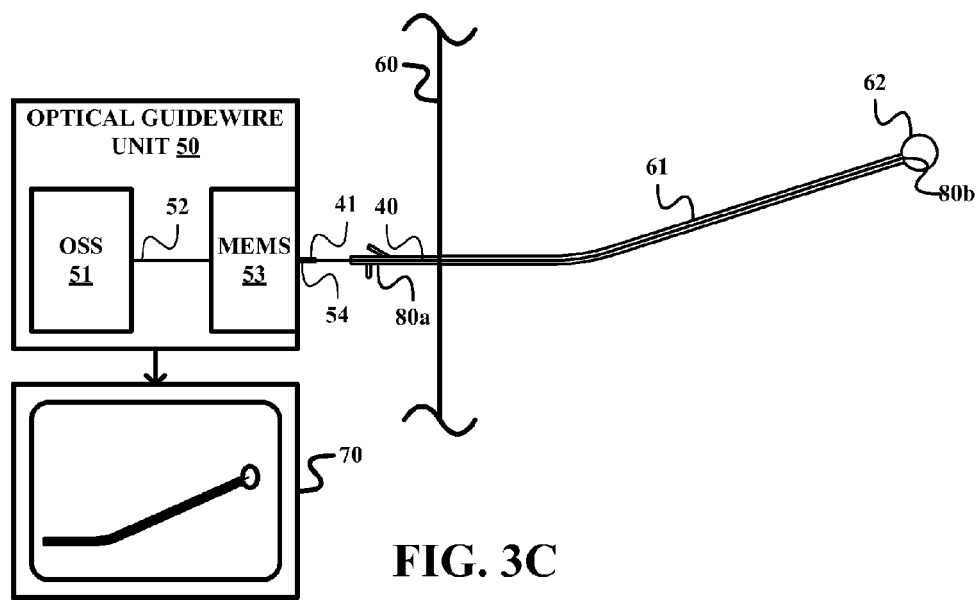

For example, as shown in FIG. 3B, a catheter 80 is backloaded upon a disconnected optical guidewire 40 whereby a distal end 80b of catheter 80 reaches target region 62 and a proximal end 80a of catheter 80 is spaced from plug 41 to enable a reconnection of plug 41 to plug 54. Thereafter, as shown in FIG. 3C, plugs 41 and 54 are snapped back together to optically couple the fiber cores of optical guidewire 40 and interface optical fiber 52 with MEMS 53 operating to facilitate a proper optical alignment of the fiber cores. As optical guidewire 40 has been previously positioned relative to target region 62, optical guidewire controller 51 operates to partially or entirely reconstruct the shape of optical guidewire 40 whereby an imaging system 70 may display an overlay of catheter loaded optical guidewire 40 within a scan image of target region 62.

In practice, variations in the structural configurations of an optical guidewire, a guidewire interface and an optical connector are neither limited nor restricted. Thus, the following descriptions of an optical guidewire, guidewire interface and optical connector as shown in FIGS. 4-8 are provided as exemplary examples of structural configurations of an optical guidewire, a guidewire interface and an optical connector.

As shown in FIG. 4A, an optical fiber 90a is suitable for incorporation in an optical guidewire or a guidewire interface. Specifically, optical fiber 90a has a cladding 91 enclosing three (3) FBG fiber cores 93a-95a oriented in a helical structure including an additional FBG fiber core 92a in a helix center. Integral with fiber cores 92a-95a are respective fiber core extensions 92b-95b enclosed by respective ferrules 96a-96d, which are ceramic, plastic or stainless steel that holds fiber core extensions 96 perpendicular to cladding 91.

Figure 4B:
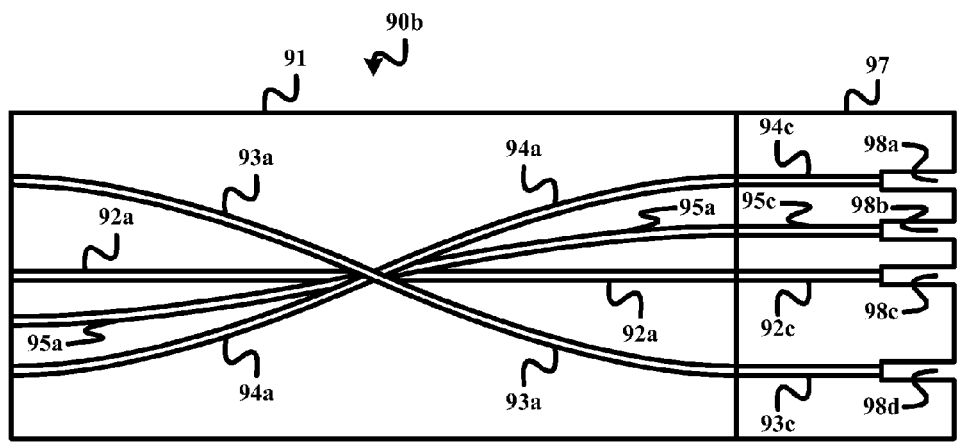

As shown in FIG. 4B, a complementary optical fiber 90b alternatively has a slotted ferrule 97 enclosing fiber core extensions 92c-95c with fiber core extensions 92c-95c being optically accessible via respective slots 98a-98d.

Figure 5B:
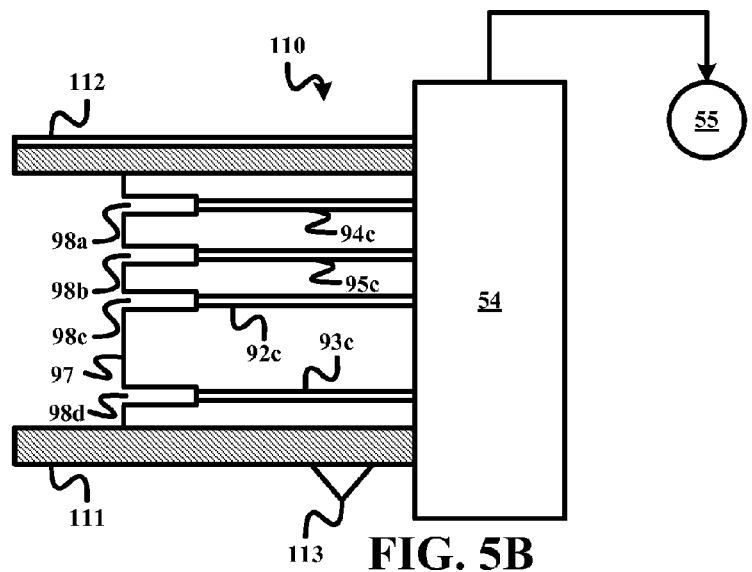

FIGS. 5A and 5B respectively illustrate optical fiber 90a (FIG. 4A) and optical fiber 90b (FIG. 4B) incorporated with an optical guidewire and a guidewire interface.

Specifically, as shown in FIG. 5A, cladding 91 of optical fiber 90a (FIG. 4A) is enclosed by a sheath 99 with a guidewire connector 100 coupled to a proximal end 91b of cladding 91. Guidewire connector 100 includes a female plug 101 spring loaded onto cladding 91 via a spring 107 and a pair of triangular posts 103 and 106 coupled to cladding 91. Posts 103 and 106 attach female plug 101 to cladding 91 and are slidable within respective channels 102 and 105. Female plug 101 further includes a wedge connector 104.

As shown in FIG. 5B, a MEMS 54 encloses optical fiber 90b (FIG. 4B) with fiber core extensions 92c-95c and ferrule 97 extending into an interface connector 110 being a male plug 111 having a beam 112 receivable within channel 102 of female plug 101 (FIG. 5A) and a wedge connector 113.

Figure 5C:
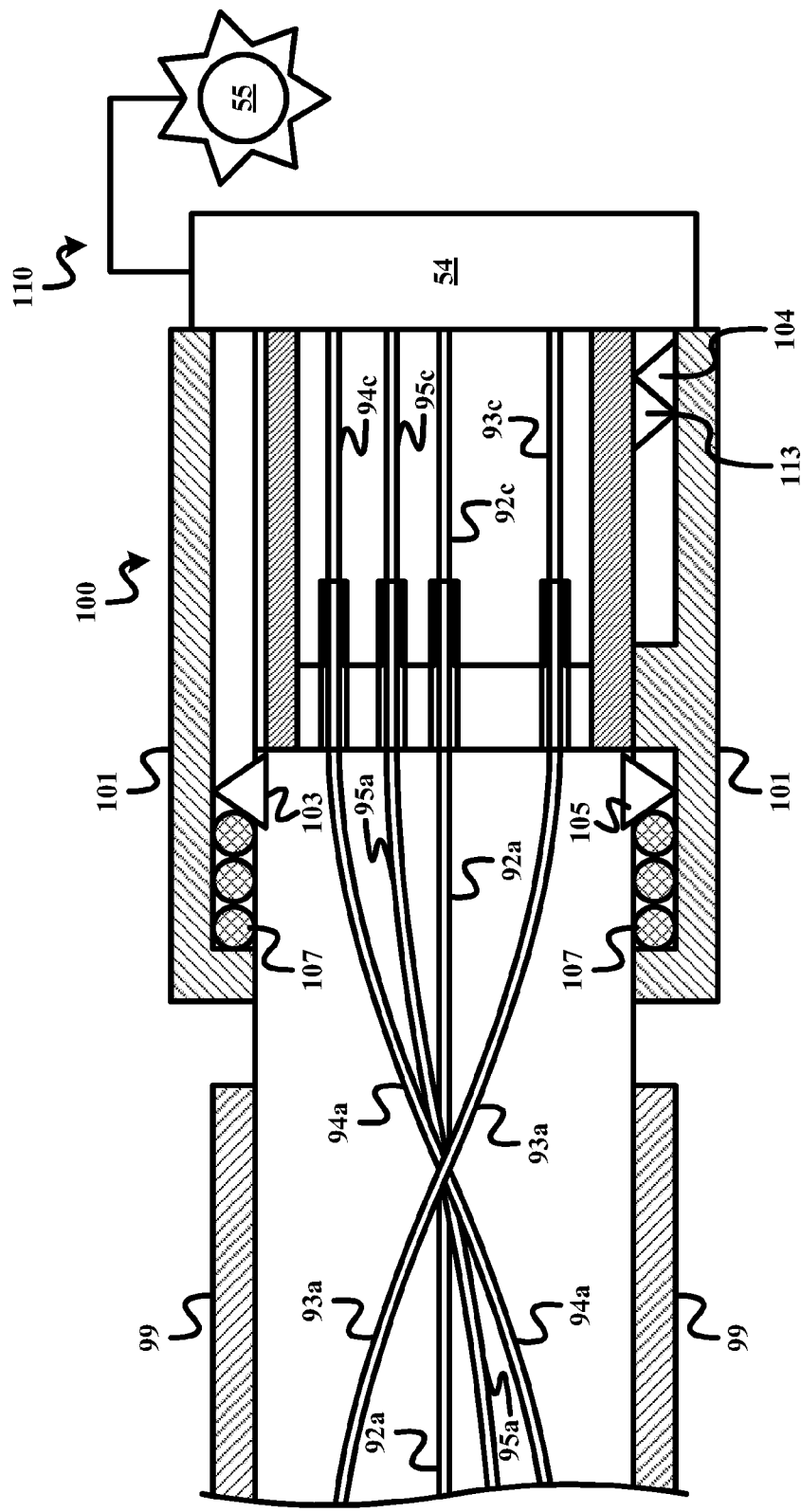

As shown in FIG. 5C, sliding beam 112 within channel 102 aligns plugs 101 and 111 whereby fiber core extensions 92b-95b slide within slotted ferrule 97 to optically couple to respective fiber core extensions 92c-95c. Wedge connectors 104 and 113 interlock to hold plugs 101 and 111 together. MEMS 54 performs an optical alignment of the fiber core extensions as needed with an indicator 55 being activated upon an proper optical alignment of the fiber core extensions.

FIGS. 6A and 6B respectively illustrate a distal end and a proximal end of optical guidewire 90a having guidewire connector 100 coupled thereto. Of importance is the diameter d of guidewire connector 100. In practice, a maximum for diameter d is 2 mm for facilitating a backloading of a catheter onto optical guidewire 90.

Also in practice, alternate embodiments of the guidewire connector cross-section may include non-circular symmetric or asymmetric, angle faceted geometries that allow for registered or keyed insertion with optical alignment guaranteed by the connector geometry at the mating interface.

For example, FIGS. 7A and 7B respectively illustrate a distal end and a proximal end of a triangular cross-section for an optical guidewire 120 having a cladding 121 supporting three (3) FBG fiber cores 123a-125a oriented in a helical structure including an additional FBG fiber core 122a in a helix center. Integral with fiber cores 122a-125a are respective fiber core extensions 122b-125b enclosed by ferrules. A sheath 129 encloses cladding 121. On the distal end as shown in FIG. 7B, guidewire connector 130 includes a female plug 131 having a channel 132 and a wedge connector 134.

For example, FIGS. 8A and 8B respectively illustrate a distal end and a proximal end of a rectangular cross-section for an optical guidewire 140 having a cladding 141 supporting three (3) FBG fiber cores 143a-145a oriented in a helical structure including an additional FBG fiber core 142a in a helix center. Integral with fiber cores 142a-145a are respective fiber core extensions 142b-145b enclosed by ferrules. A sheath 149 encloses cladding 141. On the distal end as shown in FIG. 8B, guidewire connector 150 includes a female plug 151 having a channel 152 and a wedge connector 154.

From the description of FIGS. 1-8, those having skill in the art will have a further appreciation on how to construct an optical guidewire, a guidewire interface and an optical connector in accordance with the inventive principles of the present invention for any type of minimally invasive intervention involving an advancement of a catheter to a target region via the optical guidewire.

While various exemplary embodiments of the present invention have been illustrated and described, it will be understood by those skilled in the art that the exemplary embodiments of the present invention as described herein are illustrative, and various changes and modifications may be made and equivalents may be substituted for elements thereof without departing from the true scope of the present invention. For example, although the invention is discussed herein with regard to FBGs, it is understood to include fiber optics for shape sensing or localization generally, including, for example, with or without the presence of FBGs or other optics, sensing or localization from detection of variation in one or more sections in a fiber using back scattering, optical fiber force sensing, fiber location sensors or Rayleigh scattering. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An optical guidewire system, comprising:
   an optical guidewire including,
      a guidewire configured and dimensioned for advancing a catheter over the guidewire to a target region relative to a distal end of the optical guidewire, and
      at least one guidewire fiber core integrated within the guidewire for generating an encoded optical signal indicative of a shape of the optical guidewire;
   an optical guidewire controller responsive to the encoded optical signal for reconstructing the shape of the optical guidewire;
   a guidewire interface including at least one interface fiber core optically coupled to the optical guidewire controller; and
   an optical connector for connecting the optical guidewire to the guidewire interface to optically communicate the encoded optical signal from the at least one guidewire fiber core through the at least one interface fiber core to the optical guidewire controller, and
      wherein the optical connector is configured and dimensioned for a backloading of the catheter over the optical connector onto a proximal end of the optical guidewire, and
      wherein the guidewire interface includes a microelectromechanical system operable for micro-aligning the at least one guidewire fiber core and the at least one interface fiber core.

2. The optical guidewire system of claim 1, wherein the optical guidewire further includes:
   at least one fiber core extension, each fiber core extension being integral with one of the at least one guidewire fiber core.

3. The optical guidewire system of claim 2, wherein the optical guidewire further includes:
   at least one ferrule, each ferrule at least partially enclosing one of the at least one fiber core extension.

4. The optical guidewire system of claim 2, wherein the optical guidewire further includes:
   a ferrule at least partially enclosing the at least one fiber core extension.

5. The optical guidewire of system of claim 1, wherein the guidewire interface includes:
   at least one fiber core extension, each fiber core extension being integral with one of the at least one interface fiber core.

6. The optical guidewire system of claim 5, wherein the guidewire interface further includes:
   at least one ferrule, each ferrule at least partially enclosing one of the at least one fiber core extension.

7. The optical guidewire system of claim 5, wherein the guidewire interface further includes:
   a ferrule at least partially enclosing the at least one fiber core extension.

8. The optical guidewire system of claim 1, wherein:
   the guidewire interface further includes at least one ferrule, each ferrule at least partially enclosing one of the at one interface fiber core; and
   the optical connector includes an interface connector at least partially enclosing the at least one ferrule.

9. The optical guidewire system of claim 5, wherein:
   the guidewire interface further includes a ferrule at least partially enclosing the at one interface fiber core; and
   the optical connector includes an interface connector at least partially enclosing the ferrule.

10. The optical guidewire system of claim 1, wherein the optical connector includes:
    a guidewire connector enclosing a proximal end of the optical guidewire; and
    an interface connector at least partially enclosing the guidewire interface.

11. The optical guidewire system of claim 10, wherein the guidewire connector and the interface connector are operable to snap together responsive to an optical alignment of the at least one guidewire fiber core and the at least one interface fiber core.

12. The optical guidewire system of claim 1, wherein the microelectromechanical system includes at least one of micro-actuators and Vernier latches.

13. The optical guidewire system of claim 1, wherein the guidewire interface further includes:
    an indicator operable for indicating a proper micro-alignment of the at least one guidewire fiber core and the at least one interface fiber core.

14. The optical guidewire system of claim 1, wherein the optical guidewire has a circular cross-section.

15. The optical guidewire system of claim 1, wherein the optical guidewire has a non-circular cross-section.

* * * * *